United States Patent
Patil et al.

(10) Patent No.: US 9,206,214 B2
(45) Date of Patent: Dec. 8, 2015

(54) PROCESS FOR PREPARATION OF KETOLIDE INTERMEDIATES

(75) Inventors: Vijaykumar Jagdishwar Patil, Solapur (IN); Satish Birajdar, Aurangabad (IN); Bharat Dond, Aurangabad (IN); Bharat Kalidas Trivedi, Farmington Hills, MI (US)

(73) Assignee: Wockhardt Ltd., Bandra East, Mumbai (IN)

( * ) Notice: Subject to any disclaimer, the term of this patent is extended or adjusted under 35 U.S.C. 154(b) by 11 days.

(21) Appl. No.: 14/002,316

(22) PCT Filed: Feb. 29, 2012

(86) PCT No.: PCT/IB2012/050940
§ 371 (c)(1),
(2), (4) Date: Nov. 12, 2013

(87) PCT Pub. No.: WO2012/117357
PCT Pub. Date: Sep. 7, 2012

(65) Prior Publication Data
US 2014/0073770 A1    Mar. 13, 2014

(30) Foreign Application Priority Data
Mar. 1, 2011   (IN) .................. 559/MUM/2011

(51) Int. Cl.
*C07H 1/00* (2006.01)
*C07H 17/08* (2006.01)
*C07D 493/04* (2006.01)

(52) U.S. Cl.
CPC .............. *C07H 17/08* (2013.01); *C07D 493/04* (2013.01)

(58) Field of Classification Search
CPC .......................................... C07H 17/08
See application file for complete search history.

(56) References Cited

U.S. PATENT DOCUMENTS

2004/0014691 A1 *  1/2004  Searle et al. ............. 514/29

FOREIGN PATENT DOCUMENTS

WO    WO03072588 A1   9/2003
WO    WO2008023248 A2  2/2008

* cited by examiner

*Primary Examiner* — Elli Peselev
(74) *Attorney, Agent, or Firm* — Bio Intellectual Property Services LLC (Bio IPS); O. (Sam) Zaghmout

(57) ABSTRACT

The inventions discloses a process for preparation of compounds of Formula (IX), Wherein, R is $C_1$-$C_6$ alkyl, $R_1$ is hydrogen or a hydroxyl protecting group, and $R_2$ is hydrogen or fluorine.

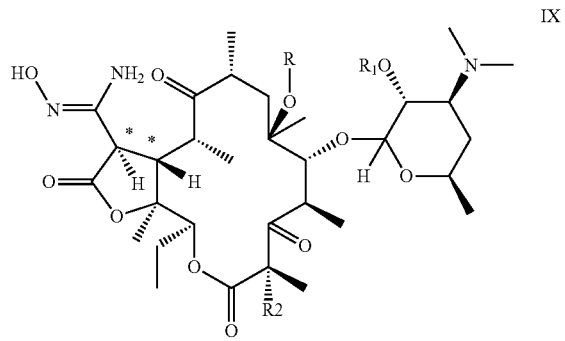

14 Claims, No Drawings

PROCESS FOR PREPARATION OF KETOLIDE INTERMEDIATES

FIELD OF THE INVENTION

The invention relates to a process for preparation of compounds of Formula (IX) useful in the synthesis of 11,12-γ lactone ketolide compounds.

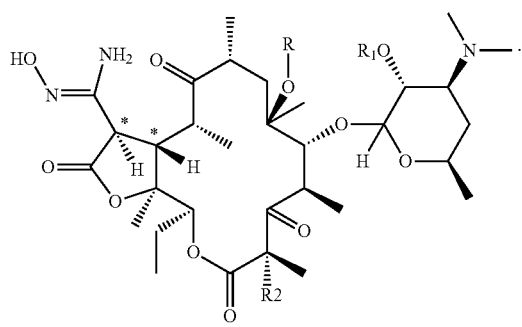

IX

Wherein,
* indicates a chiral center,
R is $C_1$-$C_6$ alkyl,
$R_1$ is hydrogen or hydroxyl protecting group, and
$R_2$ is hydrogen or fluorine.

BACKGROUND OF THE INVENTION

Macrolide compounds represent a well-known family of antibacterial agents. For example, erythromycin A, 14-membered macrolide, was isolated in 1952 from *Streptomyces erythraeus*. Examples of macrolides being used as therapeutic agents include Roxithromycin, Clarithromycin and Azithromycin (azalide). Ketolides are semisynthetic 14-membered ring macrolide derivatives, characterized by the presence of a keto function at position 3 instead of L-cladinose moiety present in the macrolactone ring. Telithromycin and Cethromycin are examples of ketolides.

U.S. Pat. No. 4,331,803 discloses 6-O-methyl derivative of erythromycin i.e. Clarithromycin. U.S. Pat. No. 4,349,545 discloses Roxithromycin. U.S. Pat. No. 4,517,359 discloses Azithromycin. Another compound, Telithromycin is described in EP 680967 A1 and corresponding U.S. Pat. No. 5,635,485 and *Bioorg. Med. Chem. Lett.* 1999, 9(21), 3075-3080. Another ketolide Cethromycin (ABT 773) is disclosed in WO 98/09978, and *J. Med. Chem.* 2000, 43, 1045.

U.S. Pat. No. 6,900,183 describes 11,12-γ lactone ketolides having C-21 of the lactone substituted with cyano or amino derivatives. Several other disclosures, including, US 2004/0077557; WO 02/16380, WO 03/42228, WO 04/16634 and WO 03/072588 disclose 11,12-γ lactone ketolides. WO 07/060518 discloses some of the intermediates useful in the synthesis of ketolides and novel ketolides.

SUMMARY OF THE INVENTION

In one general aspect, there are provided compounds of Formula (IX) or a pharmaceutically acceptable salt, solvate, hydrate, polymorph or stereoisomer thereof,

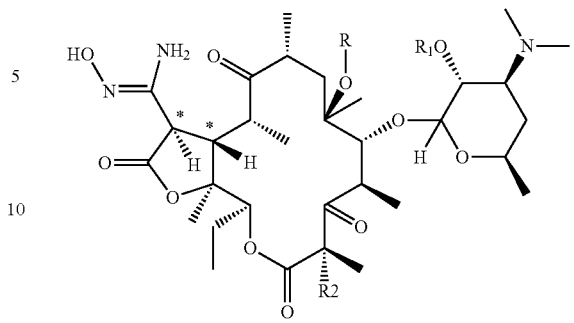

IX

Wherein,
R is $C_1$-$C_6$ alkyl,
$R_1$ is hydrogen or a hydroxyl protecting group, and
$R_2$ is hydrogen or fluorine.

In another general aspect, there is provided process for preparation of compound Formula (IX)

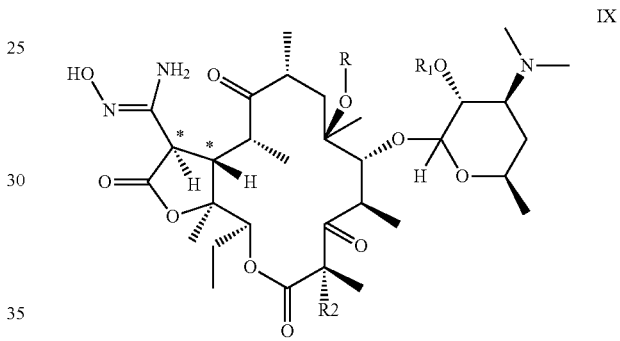

IX

Wherein,
R is $C_1$-$C_6$ alkyl,
$R_1$ is hydrogen or a hydroxyl protecting group, and
$R_2$ is hydrogen or fluorine.

In another general aspect, there is provided a process for preparation of a compound of Formula (XI)

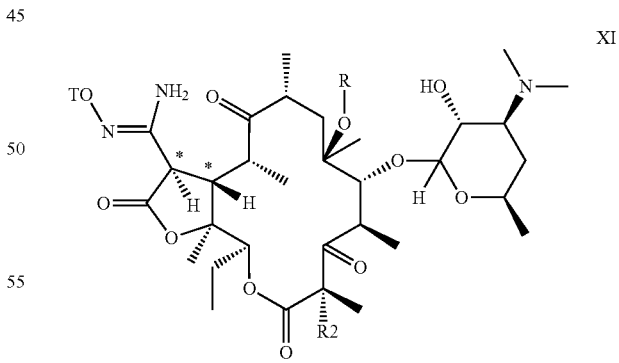

XI wherein,
T is —CH($R_3$)—P-Q wherein $R_3$ is H, unsubstituted or substituted lower alkyl or aryl,
P is heteroaryl ring,
Q is unsubstituted or substituted aryl or heteroaryl ring,
P is attached to Q via carbon-carbon link,
R is $C_1$-$C_6$ alkyl, and
$R_2$ is hydrogen or fluorine.

In yet another general aspect, there is provided a process for preparation of a compound of Formula (VIb)

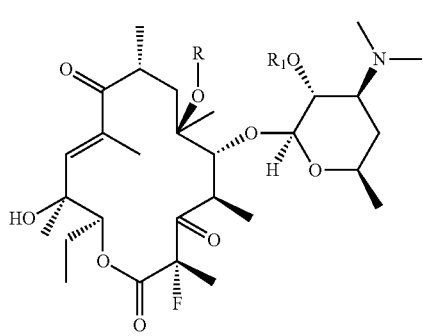

wherein,
R is $C_1$-$C_6$ alkyl, and
$R_1$ is hydrogen or hydroxyl protecting group.

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise.

In general, the following definitions are used, unless otherwise described.

The symbol* indicates chiral center in the Formula (I) which is either in the R or in S form or mixture of both forms.

The term "stereoisomer" refers to compounds, which have identical chemical composition, but differ with regard to arrangement of the atoms and the groups in space. These include enantiomers, diastereomers, geometrical isomers, atropisomer and comformational isomers. Geometric isomers may occur when a compound contains a double bond or some other feature that gives the molecule a certain amount of structural rigidity. An enantiomer is a stereoisomer of a reference molecule that is the nonsuperimposable mirror image of the reference molecule. A diastereomer is a stereoisomer of a reference molecule that has a shape that is not the mirror image of the reference molecule. An atropisomer is a conformation of a reference compound that converts to the reference compound only slowly on the NMR or laboratory time scale. Conformational isomers (or conformers or rotational isomers or rotamers) are stereoisomers produced by rotation about σ bonds, and are often rapidly interconverting at room temperature. Racemic mixtures are also encompassed within the scope of this invention. Some of the compounds of the present invention may have trans and cis isomers and geometric E- and Z-isomers. The wavy bond indicates that the compounds may be present as either of E- or Z-isomer. Also some of the compounds according to this invention may exist as diastereomers. In addition, where the process for the preparation of the compounds according to the invention give rise to mixture of stereoisomers, these isomers, may be separated by conventional techniques such as preparative chromatography and HPLC. The compounds may be prepared as a single stereoisomer or in racemic form as a mixture of some possible stereoisomer.

The term "polymorphs, solvates and hydrates" has meaning as discussed herewith. The compounds of invention may exists as different polymorphs such as crystalline or amorphous forms and as such are intended to be included in the present invention. In addition, some of the compounds may form solvates with water (i.e. hydrates), which contains various amounts of water, for instance the hydrate, hemihydrate and sesquihydrate forms. Also the compound can form solvates with common organic solvents. Such solvates and hydrates are intended to be included within the scope of this invention.

The term "lower alkyl" refers to $C_1$-$C_6$ alkyl saturated, straight or branched chain hydrocarbon radicals containing between one and six carbon atoms. Examples of $C_1$-$C_6$ alkyl radicals include but are not limited to, methyl, ethyl, propyl, butyl, pentyl, hexyl, and their branched isomers such as iso-propyl, iso-butyl or tert-butyl.

The term "cycloalkyl" refers to $C_3$-$C_6$ saturated carbocyclic radical containing between three and six carbon atoms. Examples of $C_3$-$C_6$ saturated carbocyclic radical include cyclopropyl, cyclobutyl, cyclopentyl, or cyclohexyl.

The term "substituted lower alkyl" refers to substituted $C_1$-$C_6$ alkyl, substituted by independent replacement of one or two or three of the hydrogen atoms thereon with F, Cl, Br, I, $NO_2$, $NH_2$, CN, OH, $C_1$-$C_6$ alkoxy, alkylamino, dialkylamino, mercapto, formyl, carboxy, alkoxycarbonyl and carboxamide, aryl, heteroaryl, substituted aryl, substituted heteroaryl. Examples of such substitutions are fluoromethyl, difluoromethyl, trifluoromethyl, nitromethyl, aminomethyl, cyanomethyl, hydroxymethyl and the like. Examples of $C_1$-$C_6$ alkoxy are methoxy, ethoxy, propyloxy, isopropyloxy, butyloxy, pentyloxy, hexyloxy.

The term "alkylamino" refers to a group having the structure —NH($C_1$-$C_6$ alkyl) where $C_1$-$C_6$ alkyl is as previously defined.

The term "dialkylamino" refers to a group having the structure —N($C_1$-$C_6$ alkyl) ($C_1$-$C_6$ alkyl), where $C_1$-$C_6$ alkyl is as previously defined. Examples of dialkylamino are, but not limited to, dimethylamino, diethylamino, methylethylamino and the like.

The term "aryl" refers to a mono or bicyclic ring system such as phenyl or naphthyl.

The term "heteroaryl" refers to a mono i.e. 5-6 membered or bicyclic i.e. fused aromatic ring system having at least one carbon atom of the aromatic ring replaced by an atom selected from the group of N, O, S. For example pyridyl, pyrazinyl, pyrimidinyl, pyrrolyl, pyrazolyl, imidazolyl, thiazolyl, isothiazolyl, oxazolyl, isoxazolyl, thiadiazolyl, oxadiazolyl, thienyl, triazolyl, triazinyl, furanyl, N-oxo-pyridyl, and the like. It includes the fused biaryl systems such as indolyl, quinolinyl, isoquinolinyl, benzothiazolyl, benzoxazolyl, benzothienyl, N-oxo-quinolyl, benzimidazolyl, benzopyranyl, benzoisothiazolyl, benzodiazinyl, benzofurazanyl, indazolyl, indolizinyl, benzoluryl, quinoxannyl, pyrrolopyridinyl, furopyridinyl (such as furo[2,3-c]pyridinyl, furo[3,2-b]pyridinyl, furo[2,3-b]pyridinyl), naphthyridinyl, phthalazinyl, pyridopyridyl, quinazolinyl, thienofuryl, thienopyridyl, thienotheinyl, purinyl (such as 9H-purin-1-yl, 6-amino-9H-purin-9-yl), pyridinyl-1H-pyrazol-1-yl and the like.

The aryl or the heteroaryl group can be optionally substituted by independent replacement of one or more of hydrogen atoms thereon with substituents selected from $C_1$-$C_6$ alkyl, substituted $C_1$-$C_6$ alkyl, cyano, hydroxy, halogen, amino, formyl, carboxy, carboxamide, $C_1$-$C_6$ alkoxy, $C_1$-$C_6$ thioalkoxy, $C_1$-$C_6$ alkylcarbonyl, amino, alkylamino, dialkylamino, mercapto, nitro, carboxy, alkoxycarbonyl, aminocarbonyl, alkylthio, arylthio, heteroarylthio or haloalkyl.

The term "pharmaceutically acceptable salt" as used herein refers to one or more salts of the free base of the invention which possess the desired pharmacological activity of the free base and which are neither biologically nor otherwise undesirable. The salts are suitable for use in contact with the tissues of human and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids are hydrochloric acid, nitric acid, perchloric acid, hydrobromic acid, sulphuric acid or phosphoric acid. Examples of organic acids are acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also included are the salts with various amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malonate, 2-naphthalenesulfonate, nicotinate, oleate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like.

Salt of an acid moiety in the compound can also be prepared by reacting with a suitable base. These suitable salts are furthermore those of the inorganic or organic bases. Inorganic bases such as KOH, NaOH, Ca(OH)$_2$, Al(OH)$_3$. The organic base salts from basic amines such as ethylamine, triethylamine, diethanolamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like. Further pharmaceutically acceptable salts include, when appropriate, nontoxic ammonium, quaternary ammonium, and amine cations formed using counterions such as nanue, hydroxide, carboxylate, sulfate, phosphate, nitrate, lower alkyl sulfonate and aryl sulfonate.

Abbreviations which may be used in the descriptions of the schemes and the examples that follow are: Ac for acetyl; AIBN for azobis-isobutyronitrile; Bn for benzyl; Boc for t-butoxycarbonyl; Bu$_3$SnH for tributyltin hydride; Bz for benzoyl; CDI for carbonyldiimidazole; DBU for 1,8-diazabicyclo[5.4.0]undec-7-ene; DCC for 1,3-dicyclohexylcarbodiimide; DEAD for diethylazodicarboxylate; DIC for 1,3-diisopropylcarbodiimide; DMAP for dimethylaminopyridine; DMF for dimethyl formamide; DPPA for diphenylphosphoryl azide; EtOAc for ethyl acetate; KHMDS for potassium bis(trimethylsilyl)amide; LDA for lithium diisopropyl amide; MeOH for methanol; Me$_2$S for dimethyl sulfide; MOM for methoxymethyl; NaN(TMS)$_2$ for sodium bis(trimethylsilyl)amide; NCS for N-chlorosuccinimide; NMO for 4-methylmorpholine N-oxide; PCC for pyridinium chlorochromate; PDC for pyridinium dichromate; Ph for phenyl; TEA for triethylamine; THF for tetrahydrofuran; TPP or PPh$_3$ for triphenylphosphine; TBS for tert-butyl dimethylsilyl; TMS for trimethylsilyl In one general aspect, there are provided compounds of Formula (IX) or a pharmaceutically acceptable salt, solvate, hydrate, polymorph or stereoisomer thereof

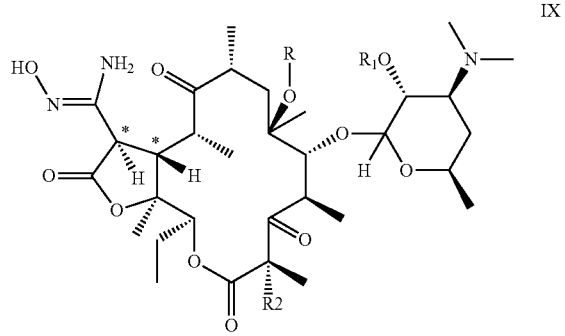

Wherein,
R is $C_1$-$C_6$ alkyl,
$R_1$ is hydrogen or a hydroxyl protecting group, and
$R_2$ is hydrogen or fluorine.

The phrase, "hydroxyl protecting group" includes a wide variety of groups capable of acting as hydroxyl protecting group. Non-limiting examples of hydroxyl protecting groups include, triethylsilyl, acetyl, benzoyl, methoxy methyl, benzyl, methoxyethoxymethyl, tertbutyldimethylsilyl groups.

In another general aspect, there is provided a process for preparation of a compound of Formula (IX)

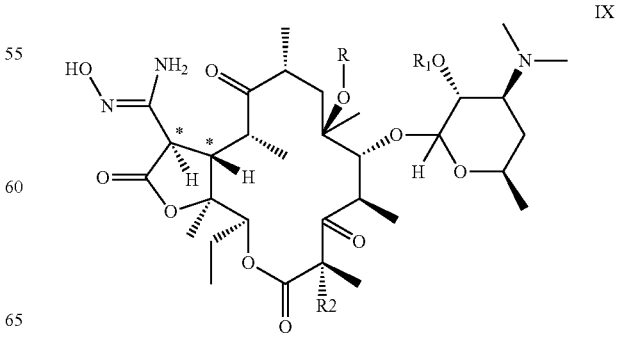

wherein,

R is $C_1$-$C_6$ alkyl, $R_1$ is hydrogen or a hydroxyl-protecting group, and $R_2$ is hydrogen or fluorine, comprising:

(a) reacting a compound of Formula (VI) with chloroacetic anhydride or chloroacetic acid, optionally in presence of a base, to obtain a compound of Formula (VII)

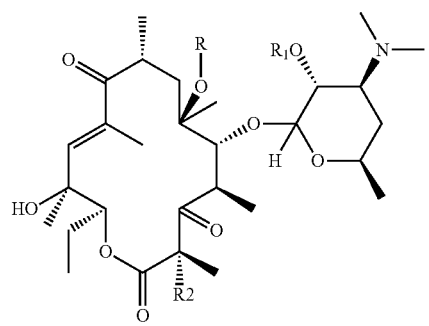

VI (b) reacting a compound of Formula (VII) with a cyanating agent in presence of a base, to obtain a compound of Formula (VIII);

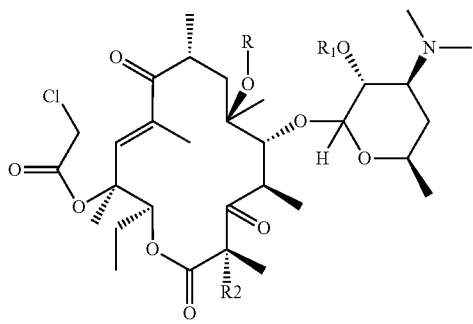

VII

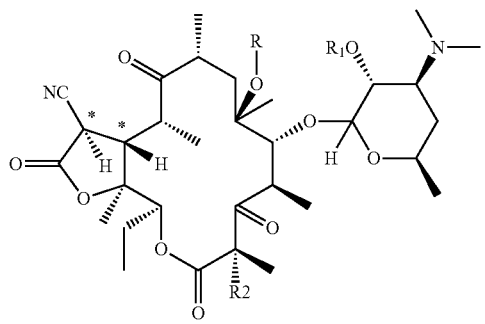

VIII (c) reacting a compound of Formula (VIII) with hydroxylamine hydrochloride in presence of a base to obtain a compound of Formula (IX);

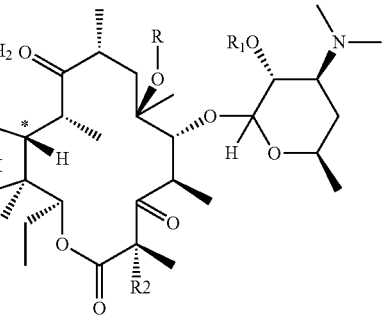

IX

Compound of Formula (VII)

In general, the compound of Formula (VI) is treated with chloroacetic anhydride or chloroacetic acid, optionally in presence of a base, to obtain a compound of Formula (VII). A wide variety of bases can be used in this reaction. Typical, non-limiting examples of bases include, bases such as pyridine, dimethylaminopyridine or a mixture of pyridine and dimethylaminopyridine.

Compound of Formula (VIII)

The compound of Formula (VII) is reacted with a cyanating agent in presence of a base to obtain a compound of Formula (VIII). Typical, non-limiting examples of cyanating agents that can be used in this reaction include sodium cyanide, potassium cyanide, copper cyanide, or tosyl cyanide. The reaction is carried out in presence of a base. Typical, non-limiting examples of bases that can be used in this reaction include sodium bicarbonate, sodium carbonate, sodium hydride, sodium-t-butoxide potassium hydroxide, potassium hydride and potassium t-butoxide.

Compound of Formula (IX)

The compound of Formula (VIII) is reacted with hydroxylamine hydrochloride in presence of a base to obtain a compound of Formula (IX). A wide variety of bases can be used in this reaction. Typical, non-limiting examples of bases includes, bases such as sodium bicarbonate, sodium carbonate, sodium hydride, sodium-t-butoxide potassium hydroxide, potassium hydride and potassium t-butoxide.

In some embodiments, there is provided a process for preparation of a compound of Formula (IX)

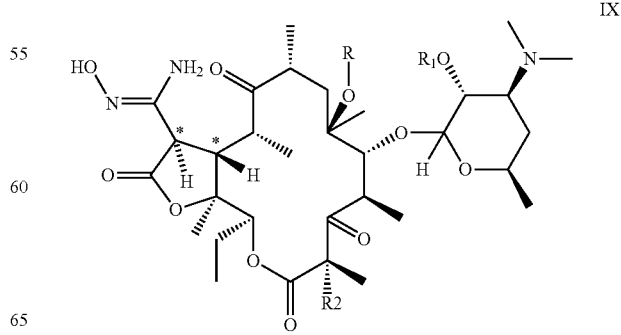

IX wherein,

R is $C_1$-$C_6$ alkyl;

$R_1$ is hydrogen or a hydroxyl-protecting group;

$R_2$ is hydrogen or fluorine;

comprising:

(a) reacting compound of Formula (VI) with chloroacetic anhydride or chloroacetic acid, optionally in presence of pyridine, dimethylaminopyridine, or a mixture of pyridine and dimethylaminopyridine to obtain a compound of Formula (VII);

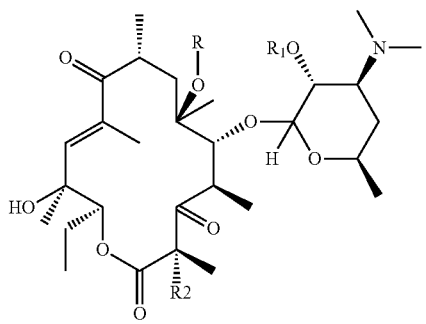

VI

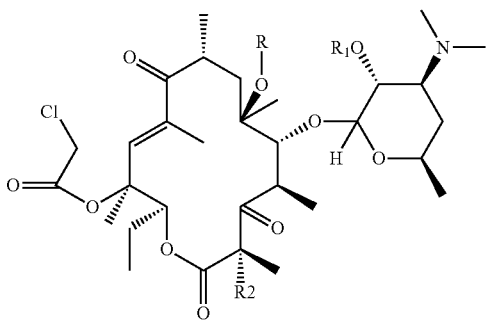

VII (b) reacting compound of Formula (VII) with potassium cyanide in presence of sodium bicarbonate in dimethylformamide, to obtain a compound of Formula (VIII);

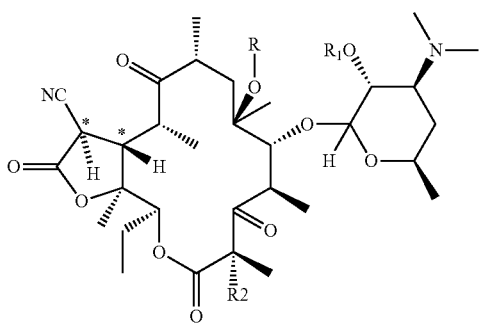

VIII (c) reacting compound of Formula (VIII) with hydroxylamine hydrochloride in presence of sodium bicarbonate in methanol, to obtain a compound of Formula (IX);

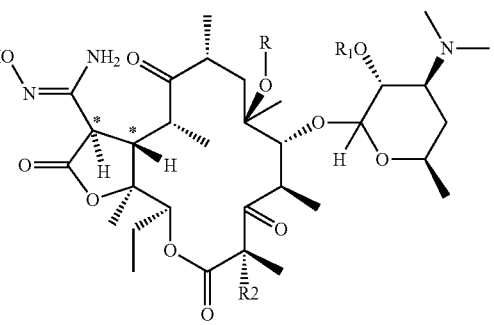

IX

In some embodiments, there is provided a process for preparation of a compound of Formula (XI)

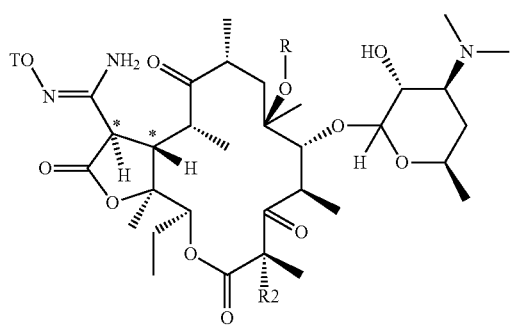

XI wherein,

T is —CH($R_3$)—P-Q wherein $R_3$ is H, unsubstituted or substituted lower alkyl or aryl, P is heteroaryl ring, Q is unsubstituted or substituted aryl or heteroaryl ring, P is attached to Q via carbon-carbon link, R is $C_1$-$C_6$ alkyl, and $R_2$ is hydrogen or fluorine comprising, (a) reacting a compound of Formula (VI) with chloroacetic anhydride or chloroacetic acid, optionally in presence of a base, to obtain a compound of Formula (VII)

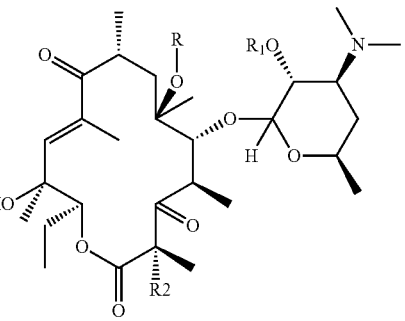

VI

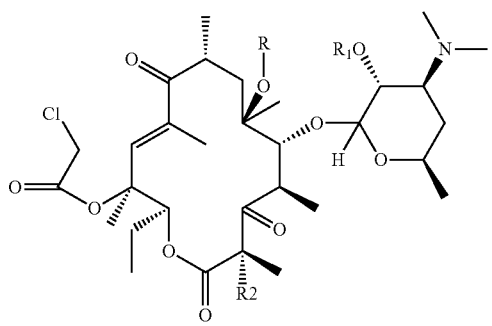

VII

Wherein,

R is $C_1$-$C_6$ alkyl, $R_1$ is hydrogen or a hydroxyl-protecting group, and $R_2$ is hydrogen or fluorine, (b) reacting a compound of Formula (VII) with a cyanating agent in presence of a base, to obtain a compound of Formula (VIII);

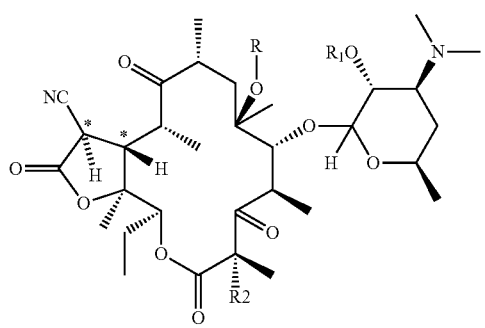

VIII (c) reacting a compound of Formula (VIII) with hydroxylamine hydrochloride in presence of a base to obtain a compound of Formula (IX);

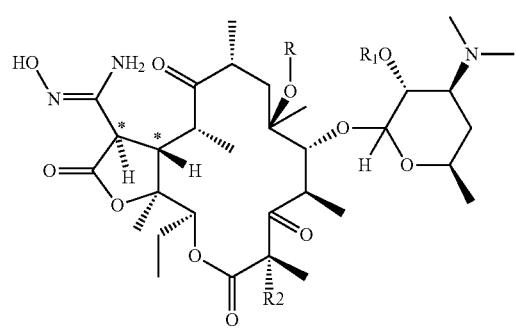

IX (d) reacting a compound of Formula (IX) with compound of Formula T-Y, wherein Y is a leaving group, optionally in presence of a base, to obtain a compound of Formula (X).

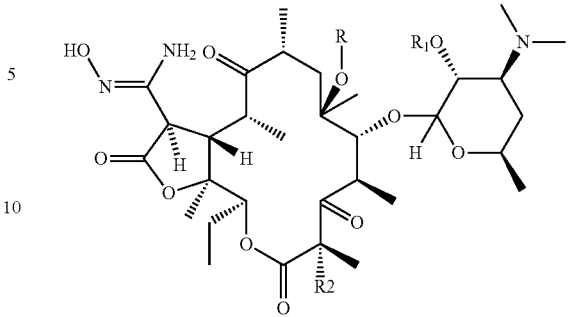

IX

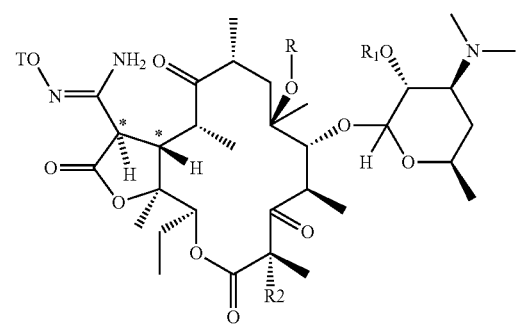

X (e) reacting compound of Formula (X) with a de-protecting agent, to obtain a compound of Formula (XI)

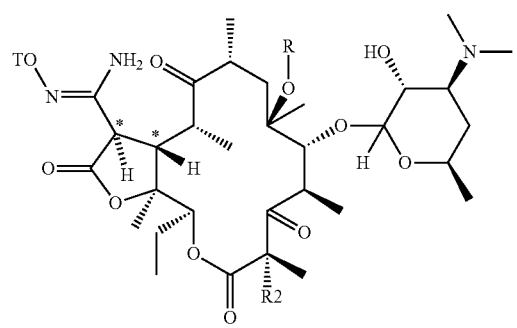

XI

Compound of Formula (X)

In general, compound of Formula (IX) is reacted with compound of Formula T-Y, optionally in presence of a base, to obtain a compound of Formula (X). A wide variety of bases can be used in this reaction. Y is a suitable leaving group. Typical, non-limiting examples of leaving groups include mesylate, tosylate, nosylate, chloride, bromide, or iodide.

Compound of Formula (XI)

In general, compound of Formula (X) is reacted with a de-protecting agent, to obtain compound of Formula (XI). A wide variety of de-protecting agents can be used in this reaction. Typical, non-limiting examples of de-protecting agents include de-protecting agent used in step (b) is selected from hydrochloric acid, sulfuric acid and pyridine hydrofluoride.

In some other embodiments, there is provided a process for preparation of a compound of Formula (VIb)

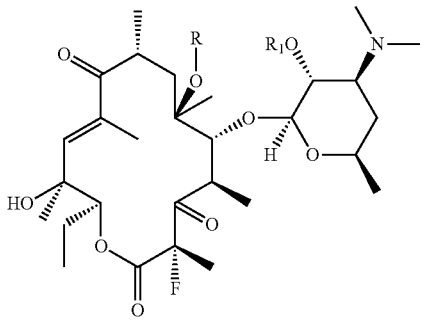

wherein,
R is $C_1$-$C_6$ alkyl, and
$R_1$ is hydrogen or hydroxyl protecting group;
Comprising, reacting a compound of Formula (VIa) with a fluorinating agent in presence of a base and a solvent, to obtain a compound of Formula (VIb).

VIa

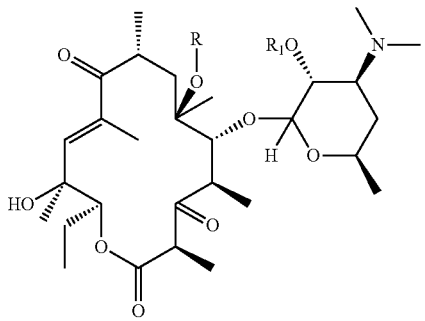

Compound of Formula (VIb)

In general, the compound of Formula (VIb) is obtained by reacting a compound of Formula (VIa) with a fluorinating agent in presence of a base and a solvent. A wide variety of fluorinating agents may be used in this reaction. Typical, non-limiting examples of fluorinating agents include one or more of N-fluorobenzenesulfonimide, 1-(chloromethyl)-4-fluoro-1,4diazobicyclo[2.2.2]octane bis[tetrafluoroborate], tetrabutylammonium fluoride and diethyl aminosulfur trifluoride. Typical, non-limiting examples of bases that can be used in this reaction include one or more of potassium-t-butoxide, potassium hydride, sodium bis(trimethylsilyl) amide, sodium hydride and sodium-t-butoxide. Typical, non-limiting examples of solvents that can be used in this reaction include one or more of dichloromethane, tetrahydrofuran, N-N-dimethylformamide and ethylene dichloride.

In some other embodiments, there is provided a process for the preparation of a compound of Formula (VIb)

VIb

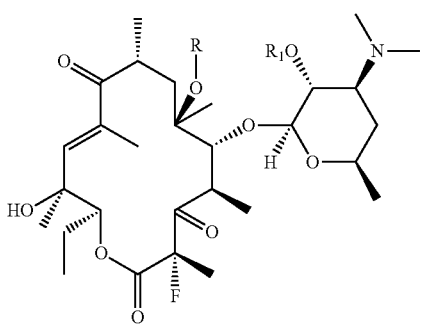

Wherein,
R is $C_1$-$C_6$ alkyl,
$R_1$ is hydrogen or hydroxyl protecting group;
comprising reacting compound of Formula (VIa) with N-fluorobenzenesulfonimide in presence of sodium-t-butoxide in tetrahydrofuran, to obtain a compound of Formula (VIb).

VIa

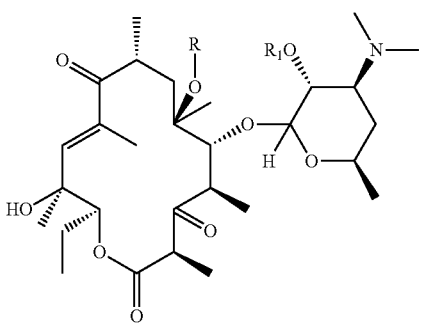

The compounds of the present invention may have trans and cis isomers and geometric E- and Z-isomers. These compounds may also exist as diastereomers. In addition, where the process for the preparation of the amidoxime compounds according to the invention give rise to mixture of stereoisomers, these isomers, may be separated by conventional techniques such as preparative chromatography. The compounds may be prepared as a single stereoisomer or in racemic form as a mixture of some possible stereoisomer.

Furthermore, some of the crystalline forms for these compounds may exist as polymorphs and as such are intended to be included in the present invention. In addition, some of the compounds may form solvates with water (i.e. hydrates) containing various amounts of water, for instance the hydrate, hemihydrate and sesquihydrate forms. Also the compounds can form solvates with common organic solvents, and such solvates are also intended to be within the scope of this invention.

GENERAL PROCEDURES (a) Synthesis of the Novel Amidoxime Core Bearing 11,12-γ-Lactone As depicted in the Scheme 1, erythromycin A, clarithromycin or derivatives of erythromycin and clarithromycin are used as the starting material for the reactions. The suitable macrolide starting material, depicted by compound (I) in the Scheme 1, is treated with an aqueous acid such as hydrochloric, sulfuric, phosphoric etc, at temperatures ranging from 0° C. to 45° C., in the presence of solvent like methanol, ethanol, isopropanol, for a period of 1 to 24 hours to obtain the intermediate (II). The intermediate (II) is then protected with a suitable protecting group such as triethylsilyl, trimethylsilyl, tert-butyldimethylsilyl, triisopropylsilyl, benzyl, allyl, acetyl, benzoyl, pivalolyl and the likes in the presence of a suitable base like triethyl amine, triisopropyl amine, pyridine, N,N-dimethyl aniline, in a solvent like, DCM, EDC, hexane, ethyl acetate etc. at a temperature starting from 0° C. to 45° C., for a period of 2-6 hours to obtain the intermediate (III). The intermediate (III) is then reacted with triphosgene in a suitable solvent such as dichloromethane, in the presence of base like pyridine to provide the 11,12-carbonate intermediate (IV), wherein R, $R_1$ have the same meaning defined in Formula (I). The conversion of the 3-hydroxy group to 3-ketone in intermediate (IV) is accomplished by using a Corey-Kim oxidation with N-chlorosuccinimide-dimethyl sulphide (NCS-DMS) or a Moffat oxidation with carbodiimide-dimethylsulphoxide (DMSO) complex in the presence of pyridinium trifluoroacetate or Dess-Martin periodinane. Such name reactions are carried out according to general procedures described in the art. In a preferred embodiment, the compound IV is dissolved in a chlorinated solvent such as dichloromethane or chloroform and to this at about 10 to 25° C. Dess-Martin periodinane reagent was added and stirred at an ambient temperature for about 0.5 to 1 hour to get the corresponding 3-ketone intermediate (V). The intermediate (V) is dissolved in solvent such as ethyl acetate or acetonitrile or tetrahydrofuran or mixtures thereof, preferably in ethyl acetate and treated with a strong base such as 1,8-diazabicyclo[5.4.0]undec-7-ene at 50-80° C., preferably at 70° C. from 2-12 hour to give intermediate (VIa).

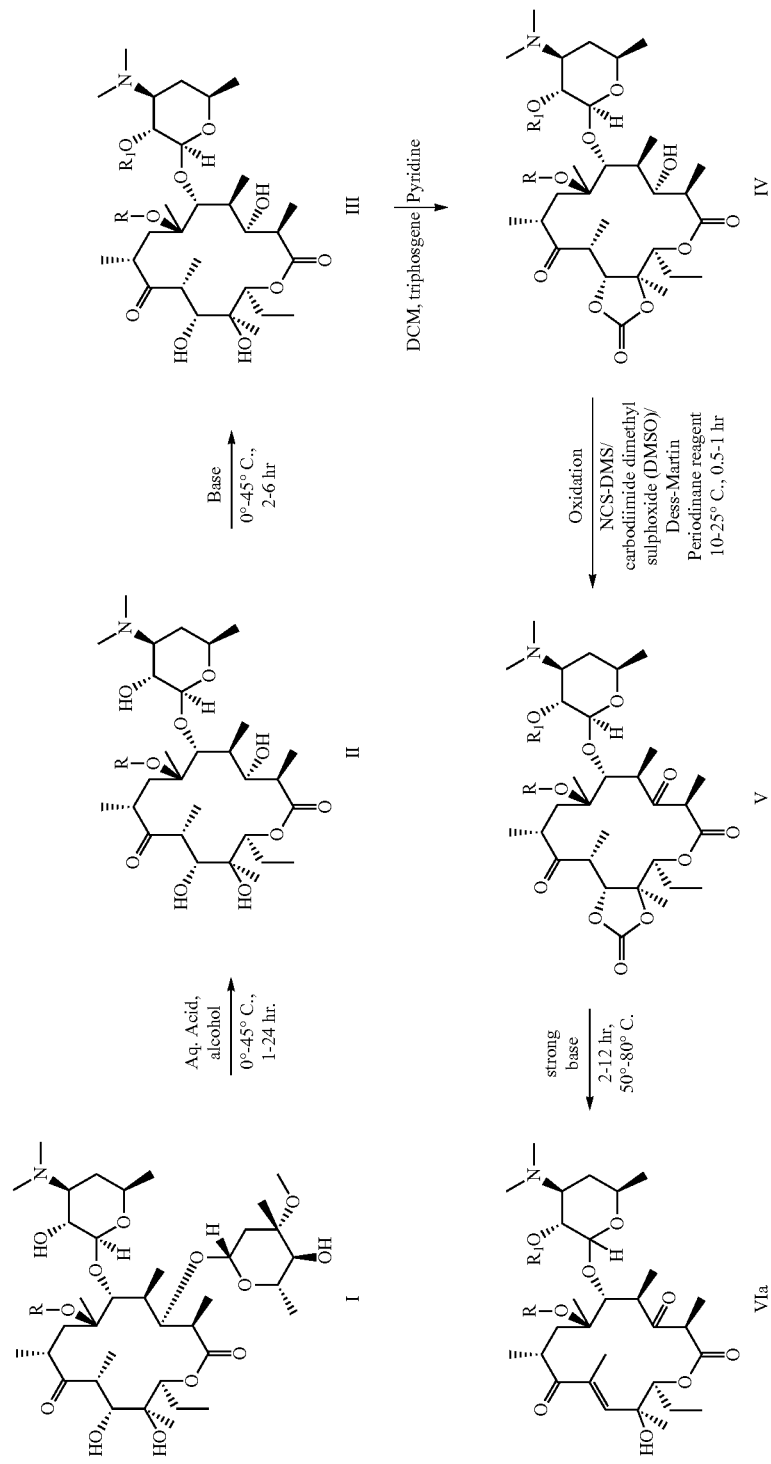

As depicted in the Scheme 2, the intermediate VIa/VIb (where, $R_2$ is hydrogen or fluorine) is dissolved in solvent such as dichloromethane or acetonitrile or tetrahydrofuran or N,N-dimethylformamide or mixtures thereof preferably in dichloromethane and treated with chloroacetic anhydride in presence of a base such as pyridine and dimethylamino pyridine or treated with chloroacetic acid in the presence of EDC, HOBt at 5-40° C., to give the intermediate (VII). The intermediate (VII) is dissolved in a solvent such as acetonitrile or tetrahydrofuran or N,N-dimethylformamide or DMSO or mixture thereof, preferably in N,N-dimethylformamide and treated with sodium cyanide or potassium cyanide or tosyl cyanide or copper cyanide at 15-40° C., to give the intermediate (VIII). The intermediate (VIII) is dissolved in solvent such as tetrahydrofuran or methanol or ethanol or mixture thereof preferably in methanol and treated with hydroxylamine hydrochloride at temperatures from 10-70° C. in the presence of base such as sodium bicarbonate or sodium carbonate or sodium hydride or sodium-t-butoxide or potassium hydroxide or potassium hydride or potassium-t-butoxide, preferably in the presence of sodium bicarbonate to give compound IX.

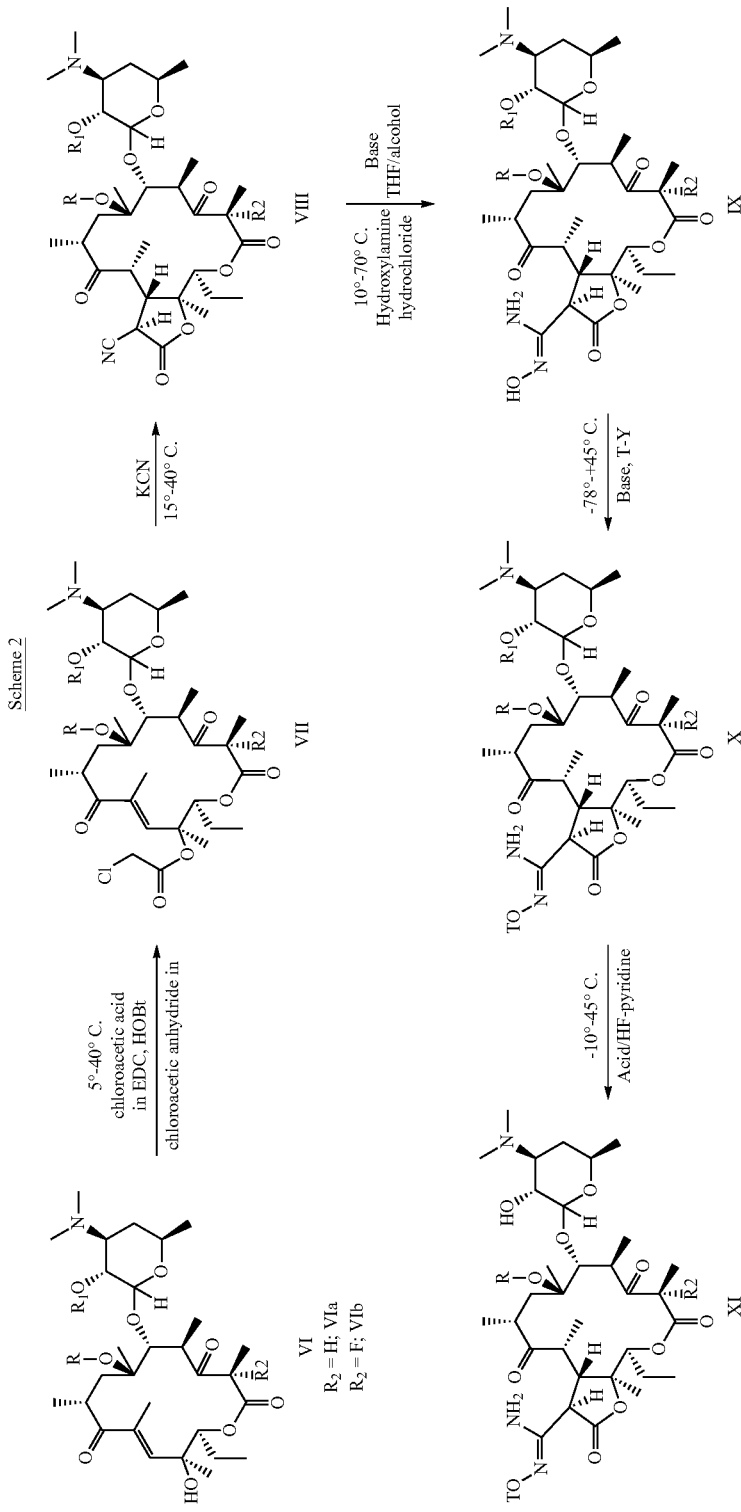

(b) Synthesis of the Novel 3-Fluoroamidoxime Core Bearing 11,12-γ-Lactone

Fluorination at the C-2 position, can be achieved by using a fluorinating reagent, such as N-fluorobenzenesulfonimide (NFSI), 1-(chloromethyl)-4-fluoro-1,4 diazoniabicyclo[2.2.2]octane bis[tetrafluoroborate] (SELECTFLUOR™), diethyl aminosulfur trifluoride, in the presence of a base to give compound (VIb).

Typically the intermediate (VIa, scheme-3) was treated with either SELECTFLUOR™ in the presence of sodium hexamethyldisilazane in DMF or N-fluorobenzenesulfonimide with potassium t-butoxide as the base in tetrahydrofuran. The reaction was conducted at temperature ranging from −78° C. to +60° C., preferably at −78° C. to −50° C. for time 5 min. to 24 hours, preferably 15 hours to give the compound (VIb).

As depicted in Scheme-3 the intermediate (VIa) is treated with a fluorinating agent like NFSI, tetrabutylammonium fluoride, DAST, in solvents like DCM, EDC, THF, DMF in the presence of a base like potassium hydride, sodium bis(trimethylsilyl)amide, sodium hydride, Potassium tert-butoxide, sodium tert-butoxide, at temperatures ranging from −50° C. to 50° C. to give intermediate (VIb, where R is C1-C6 alkyl, R1 is TES).

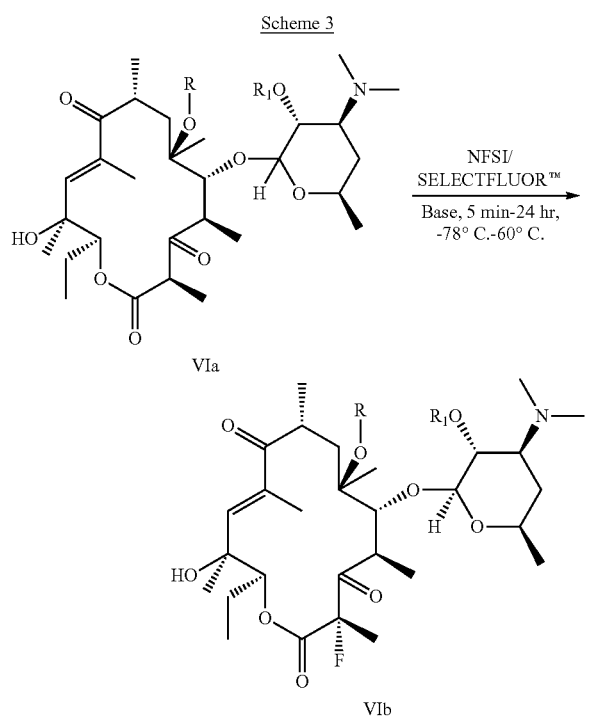

Scheme 3

(c) Use of the Cores to Synthesize Desired Ketolides

The obtained core is further manipulated to obtain the desired ketolides. O-Alkylation of this core (compound IX) is carried out with an alkylating agent like T-Y. C*H(R$_3$)—P-Q wherein the Y is a suitable leaving group like mesylate, tosylate, nosylate, chloride, bromide, iodide and T is the side chain containing R$_3$, P and Q as explained above, at temperatures ranging from −78° C. to +45° C. in the presence of a base like sodium hydride, potassium hydride sodium tert-butoxide, potassium-tert butoxide, in a solvent like THF or Toluene or DMF to obtain the intermediate X. The protecting group (R1=TES) in the Intermediate X is then deprotected by using dilute mineral acid like HCl, H$_2$SO$_4$ or a de-protecting agent like HF-pyridine in solvent like DCM or Acetonitrile or THF at temperatures ranging from −10° C. to +45° C., to obtain the final ketolide XI wherein, the side chain T is as defined above.

EXPERIMENTAL

Preparation of Amidoxime Core

Step-1: 5-O-Desosaminyl-6-O-methylerythronolide

To a solution of 0.1 N aqueous hydrochloric acid (3600 ml), Clarithromycin (200 gm, 0.267 mol) was added followed by methanol (300 ml) and the mixture was stirred at room temperature for 16-17 hours. The pH of the reaction mixture was adjusted to 10-11 with aqueous 2N NaOH solution (200 ml). The resulting mixture was stirred for 15-20 minutes and the separated solid filtered under suction. The residual solid was washed with water (2×400 ml). The solid was dried at RT for 14 hours to obtain the product as a colorless powder, 152 gm. Yield: 96%. (M.P.: 235-238° C., Mass: m/z 590 (M+H)+, Molecular Formula —C30H55NO10).

Step-2: 2'-O-TES-6-O-methyl-erythromycin

To a solution of intermediate-1 (150 gm, 0.254 mol.) in hexane (1.5 Lit) triethylamine (158.8 ml, 1.141 mol.), DMAP (62 gm, 0.508 mol.) were added successively, under nitrogen atmosphere. The resulting mixture was warmed to 45° C. and Triethyl chlorosilane (156.5 ml, 0.932 mol.) was added dropwise in 20 minutes. The reaction mixture was stirred at 45° C. for 2 hours. The resulting mixture was cooled to RT and then diluted with water (500 ml). The organic layer was separated and the aqueous layer was extracted with additional hexane (500 ml). The combined organic layer was washed with aqueous sat. NH$_4$Cl solution (500 ml). The solvent was evaporated under reduced pressure and the residue was treated with n-pentane (500 ml) and the mixture stirred for 15 minutes. The separated solid was filtered under suction and the residue washed with n-pentane (100 ml). The obtained solid was dried at RT for 10 hours to obtain the intermediate-2, as white powder 159 gm, yield: 89% (M.P. 95-98° C. Mass: m/z 704 (M+H)+, Molecular Formula —C36H69NO10Si).

Step-3: 11,12-Carbonate-2'-O-TES-11,12-dideoxy-6-O-methyl-erythromycin

A solution of intermediate 2 (138 gm, 0.196 mol.) in anhydrous DCM (1380 ml) containing pyridine (95 ml, 1.177 mol.) was cooled to −10° C., and a solution of triphosgene (72.70 gm, 0.244 mol) in DCM (207 ml) was added under nitrogen atmosphere. The reaction mixture was further stirred at 0° C. for 2 hours. The resulting mixture was neutralized with an aqueous solution of saturated NaHCO$_3$ (2.0 Lit). The organic layer was separated and washed with brine (500 ml). The solvent was evaporated under reduced pressure. The residue was triturated with n-pentane (400 ml). The separated solid was filtered under suction and washed with additional n-pentane (50 ml). The solid was further dried at RT to obtain intermediate-3, as white powder, 136 gm, and 95% yield (MP: 221-225° C.; Mass: m/z 730 (M+H); Molecular Formula —C37H67NO11Si).

Step-4: 11,12-Carbonate-2'-O-TES-11,12-dideoxy 3-O-decladinosyl-6-O-methyl-3-oxo-erythromycin To a solution of N-chloro succinimide (199 gm, 1.49 mol.) in anhydrous DCM (1.450 Lit.), dimethyl sulphide (181.8 ml, 2.47 mol) was slowly added, at −10° C. The resulting mixture was stirred at −10° C. for 1 hour and then cooled to −40° C. A solution of intermediate-3 (145 gm, 0.198 mol) in DCM (1.74 Lit.)] Was added slowly (0.5 h). The resulting mixture was stirred for 3 hours at −40° C., and quenched with triethyl amine (275 ml, 1.98 mol). The resulting mixture was diluted with aqueous saturated NaHCO$_3$ solution (1.45 Lit.). The organic layer was separated and the aqueous layer extracted with fresh DCM (1.45 Lit). The combined organic layers were evaporated under reduced pressure. To the residual mass, water (500 ml) was added and the mixture stirred for 30 min and the separated solid filtered. The same treatment of water was given three times (3×500 ml). The solid was dried at RT for 16 hours to obtain title intermediate-4 as white powder, 144 gm, yield: 99% (HPLC of this crude material showed the purity of ~73% A purified sample gave the following Data: M.P.: 160-165° C.; MS: 728 (M+H); Molecular Formula —C37H65NO11Si).

Step-5. 2'-O-TES-3-decladinosyl-11-deoxy-10,11-didehydro6-O-methyl-3-oxo-erythromycin To a solution of intermediate-4 (144 gm, 0.197 mol.) in acetone (865 ml), DBU (65 ml, 0.434 mol.) was added at room temperature. The resulting mixture was stirred at 55-58° C. for 3 hours. The solution was allowed to cool to room temperature and the solvent evaporated under reduced pressure. To the residual mass, water (800 ml) was added and the mixture stirred for 30 min. The separated solid was filtered. The solid was subjected to two more water washes. (2×800 ml). The solid was dried at RT for 16 hours to obtain the intermediate-5, as white powder, 131 gm, yield: 97% (M.P. 90-93° C.; M.S. 684 (M+H); Molecular Formula —C36H65NO9Si).

Step-6: 12-chloroethanoyl-2'-O-TES-3-decladinosyl-11-deoxy-10,11-didehydro6-O-methy-3-oxo-erythromycin To a cooled solution of chloroacetic acid (2.87 gm, 0.0306 mol.) in anhydrous DCM (56 ml) at −5° C. a solution of DCC (6.31 gm, 0.0306 mol in 21 ml of DCM) was slowly added and the solution was stirred for 45 minutes under nitrogen atmosphere. A solution of intermediate-5 [(7 gm, 0.0102 mol) in DCM (21 ml)] was slowly added followed by addition of DMAP (0.622 gm, 0.0051 mol.). The resulting mixture was stirred for 4 hour at −5 to 0° C. The solution was allowed to warm to room temperature and the solvent evaporated under reduced pressure. The residue was diluted with acetonitrile (7 ml) and the solution was extracted with hexane (3×25 ml). The hexane extract was evaporated under reduced pressure to obtain intermediate-10, as a white powder, 5.4 gm, yield: 70% (M.P. 119-122° C.; M.S.: 760 (M+H); Molecular Formula —C38H66ClNO10Si).

Step-7: (11S,21R)-2'-O-TES-3-decladinosyl-11,12-dideoxy-6-O-methyl-12,11-[oxycarbonyl-cyano)-methylene]-3-oxo-erythromycin To a solution of intermediate-10 (5.3 gm, 0.0069 mol.) in anhydrous DMF (18.5 ml) potassium cyanide (0.681 gm, 0.00104 mol) was added in one lot under nitrogen atmosphere. The reaction mixture was stirred at room temperature for 16 hours. The mixture was diluted with DCM (45 ml), aqueous saturated NaHCO$_3$ solution (75 ml) and 20% aqueous ferrous sulphate solution (38 ml). The resulting mixture was stirred for 4 hr at room temperature. The DCM layer was separated and the aqueous layer was re-extracted with extracted with DCM (2×45 ml). The combined organic layers were washed with 10% aqueous ferrous sulphate solution (75 ml). The solvent was evaporated under reduced pressure and to the residue chilled methanol (5 ml) was charged and the mixture stirred for 30 minutes at 10° C. The separated solid was filtered, washed with additional chilled methanol (1 ml). The solid was dried at RT for 10 hours to obtain the intermediate-11, as a white powder 1.84 gm, in 40% yield (M.P. 207-210° C.; M.S.: 751 (M+H); Molecular Formula —C39H66N2O10Si).

Step-8: (11S,21R)-2'-O-TES-3-decladinosyl-11,12-dideoxy-6-O-methyl-12,11-[oxycarbonyl-(21R-amidoxime-)-methylene]-3-oxo-erythromycin To a solution of hydroxylamine hydrochloride (0.841 gm, 0.0121 mol.) in anhydrous methanol (12.75 ml), sodium bicarbonate (1.22 gm, 0.0145 mol.) was added under nitrogen atmosphere. The mixture was stirred for 5-10 minutes and intermediate-11 (1.82 gm, 0.00242 mol.) was added in one lot. The resulting mixture was stirred for—24 hr. The solvent evaporated under reduced pressure and the residue diluted with water (25 ml). The resulting mixture was stirred for 15 minutes, filtered and washed with water (5 ml). The solid was dried for 1.5 hours under reduced pressure to obtain the intermediate compound—12, as a white powder, 1.86 gm, yield: 98% (M.P. 145-147° C.; M.S.: 784 (M+H); Molecular Formula —C39H69N3O11Si).

Preparation of Fluoro Amidoxime Core

Step-6: 2'-O-TES-2-Fluoro-3-decladinosyl-11-deoxy-10,11-didehydro6-O-methyl-3-oxo-erythromycin To a solution of intermediate-5 (128 gm, 0.187 mol.) in DMF (2.56 Lit.) and cooled to −40° C. Sodium t-butoxide (21.5 gm, 0.223 mol) was charged at −40° C. and after 5 minutes, under nitrogen atmosphere a solution of N-Fluoro dibenzene sulfonimide [(64.81 gm (0.205 mol) in DMF 896 ml)] was slowly added. The resulting mixture was stirred for 5-10 minutes at −40° C. The reaction mixture was quenched with an aqueous saturated NH4Cl solution (1.28 Lit) and further diluted with water (17.28 Lit.). The separated solid was filtered and the residue washed with water (512 ml). The solid was dried at RT to obtain intermediate 6, as off-white powder, 101 gm, yield: 77% (M.P.: 132-135° C. (of column purified sample); M.S. 702 (M+H); Molecular Formula —C36H64FNO9Si)

Step-7: 12-chloroethanoyl-2'-O-TES-2-Fluoro-3-decladinosyl-11-deoxy-10,11-didehydro6-O-methyl-3-oxo-erythromycin To a cooled solution of chloroacetic acid (51 gm, 0.540 mol.) in anhydrous DCM (760 ml) at −5° C., a solution of DCC (111.4 gm, 0.539 mol, in 235 ml of DCM was slowly added and the solution was stirred for 45 minutes under nitrogen atmosphere. A solution of intermediate-6 (95 gm, 0.135 mol) in DCM (235 ml) was slowly added, followed by addition of DMAP (8.235 gm, 0.0675 mol.). The resulting mixture was stirred for 1-2 hour at −5 to 0° C. The resulting solution was allowed to reach to room temperature and the solvent evaporated under reduced pressure. The residual reaction mixture was oilmen witn an aqueous saturated NaHCO$_3$ solution (400 ml) and extracted with hexane (1.0 L). The organic layer was separated and washed with aqueous saturated NH$_4$Cl solution (400 ml), with brine (200 ml). The solvent was evaporated under reduced pressure. To the concentrated mass acetonitrile (100 ml) was charged at −10° C. and the resulting mixture stirred for 2 hours at −10° C. The separated solid was filtered, under suction and the residue was washed with chilled acetonitrile (25 ml). The solid was dried at RT for 16 hours to obtain intermediate 7, as a white powder, 84 gm, yield: 80% (M.P. 136-140° C.; M.S.: 778 (M+H); Molecular Formula —C38H65ClFNO10Si).

Step-8: (11S,21R)-2'-O-TES-2-Fluoro-3-decladino-syl-11,12-dideoxy-6-O-methyl-12,11-[oxycarbonyl-(cyano)-methylene]-3-oxo-erythromycin To a solution of intermediate-7 (82 gm, 0.105 mol.) in anhydrous DMF (287 ml) potassium cyanide (12.3 gm, 0.189 mol.) was added in one portion, under nitrogen atmosphere and the resulting mixture was stirred at room temperature for 16 hours. The reaction mixture was diluted with DCM (700 ml), aqueous saturated NaHCO$_3$ solution (1.15 Lit.) and 20% aqueous ferrous sulfate solution (580 ml). The resulting mixture was stirred for 4 hours at room temperature. The organic layer was separated and the aqueous layer was re-extracted with DCM (2×700 ml). The combined organic layer was washed with 10% aqueous ferrous sulfate solution (2×400 ml). The solvent was evaporated under reduced pressure and to the residual mass water (200 ml) was added & stirred for 30 minutes. The separated solid was filtered and washed with water (100 ml). The solid was purified by column chromatography (eluting with: 5% acetone in hexane), the combined fractions were concentrated to obtain a solid. To this solid methanol (100 ml) was charged and the mixture cooled to 0-5° C. with stirring. After 2 hours at 0-5° C., the separated solid was filtered under suction and the residual solid washed with chilled methanol (25 ml). The solid was dried at RT for 10 h to obtain the intermediate-8 as a white powder. 47 gm, yield: 58% (M.P.: 190-192° C.; M.S.: 769 (M+H); Molecular Formula —C39H65FN2O10Si).

Step-9: (11S,21R)-2'-O-TES-2-Fluoro-3-decladino-syl-11,12-dideoxy-6-O-methyl-12,11-[oxycarbonyl-(21R-amidoxime-)-methylene]-3-oxo-erythromycin To a solution of hydroxylamine hydrochloride (20.35 gm, 0.439 mol.) in anhydrous methanol (270 ml) sodium bicarbonate (29.5 gm, 0.529 mol.) was added under nitrogen atmosphere. The mixture was stirred for 5-10 minutes and intermediate-8 (45 gm, 0.0585 mol.) was charged. The resulting mixture was stirred for 24 hours. The solvent was evaporated under reduced pressure. And the residue diluted with water (200 ml). The resulting mixture was stirred for 10 minutes and the separated solid filtered under suction. The residue was washed with additional water (50 ml). The solid was further purified by column chromatography (elution with: 12.5% acetone in hexane). The combined fractions were concentrated under reduced pressure to obtain compound-9, as a white powder, 40.35 gm, yield: 86% (M.P.: 184-188° C.; M.S.: 802 (M+H); Molecular Formula —C39H68FN3O11Si)

Synthesis of Ketolides

General procedure

Step-I: O-alkylation

To a stirred solution of potassium hydride (1.1 mmol, 30% suspension in mineral oil), in tolune (60 vol) at RT are added successively the 18-crown-6-ether (0.15 mmol) and amidoxime core or fluoroamidoxime core (1.0 mmol). The resulting solution is stirred for 5 minutes at RT and cooled to the required temp. A solid alkylating agent or side chain (1.2 mmol) is then added in small portions. The reaction mixture is further stirred at the required temp for 5-300 minutes (as required). The reaction mixture is then quenched by adding aqueous saturated ammonium chloride solution (5 vol). The mixture was extracted with ethyl acetate (10 vol×2). Layers are separated and the combined organic layers evaporated under reduced pressure to obtain the crude product. This is further purified by column chromatography (5-20% acetone: hexane) to obtain 2'-O-triethylsilyl protected ketolide as a step-I compound.

Step-II: Deprotection of TES

To a solution of step-I product (1.0 mmol) in acetonitrile (10 vol) a 70% HF-pyridine solution (1.5 mmol) is added and the resulting solution stirred at 30° C. for required time under N$_2$ atmosphere. Saturated aqueous sodium bicarbonate solution (5 vol) is then added to the reaction mixture and further stirred for 15 minutes. The resulting mixture is concentrated to one fourth of its volume under reduced pressure. The resulting suspension is diluted with cold water (5 vol) and the suspension stirred for 15 minutes. The separated solid is filtered under suction. The wet cake is further washed with water (10 vol.) and followed by diethyl ether (2 vol.). The residue is dried under reduced pressure to obtain the product.

Using the above procedures, the following examples were synthesized 1. (11S,21R)-3-Decladinosyl-11,12-dideoxy-6-O-methyl-3-oxo-12,11-{oxycarbonyl-[E-(N-(2-(pyridin-2-yl)-1,3,4-thiadiazol-5-yl)-methyloxy)-carboximidino-methylene]}-erythromycin A:
2. (11S,21R)-3-Decladinosyl-11,12-dideoxy-2-fluoro-6-O-methyl-3-oxo-12,11-{oxycarbonyl-[E-(N-(2-(pyridin-2-yl)-1,3,4-thiadiazol-5-yl)-methyloxy)-carboximidino-methylene]}-erythromycin A:
3. (11S,21R)-3-Decladinosyl-11,12-dideoxy-6-O-methyl-3-oxo-12,11-{oxycarbonyl-[E-(N-(2-(pyrimidin-2-yl)-1,3,4-thiadiazol-5-yl)-methyloxy)-carboximidino-methylene]}-erythromycin A:
4. (11S,21R)-3-Decladinosyl-11,12-dideoxy-2-fluoro-6-O-methyl-3-oxo-12,11-{oxycarbonyl-[E-(N-(2-(pyrimidin-2-yl)-1,3,4-thiadiazol-5-yl)-methyloxy)-carboximidino-methylene]}-erythromycin A:
5. (11S,21R)-3-Decladinosyl-11,12-dideoxy-6-O-methyl-3-oxo-12,11-{oxycarbonyl-[E-(N-(2-(pyrazin-2-yl)-1,3,4-thiadiazol-5-yl)-methyloxy)-carboximidino-methylene]}-erythromycin A:
6. (11S,21R)-3-Decladinosyl-11,12-dideoxy-2-fluoro-6-O-methyl-3-oxo-12,11-{oxycarbonyl-[E-(N-(2-(pyrazin-2-yl)-1,3,4-thiadiazol-5-yl)-methyloxy)-carboximidino-methylene]}-erythromycin A:
7. (11S,21R)-3-Decladinosyl-11,12-dideoxy-6-O-methyl-3-oxo-12,11-{oxycarbonyl-[E-(N-(2-(pyridin-2-yl)-1,3,4-thiadiazol-5-yl)-ethyl-1-oxy)-carboximidino-methylene]}-erythromycin A:
8. (11S,21R)-3-decladinosyl-11,12-dideoxy-2-fluoro-6-O-methyl-3-oxo-12,11-{oxycarbonyl-[E-(N-(2-(pyridin-2-yl)-1,3,4-thiadiazol-5-yl)-(S)-ethyl-1-oxy]-carboxamidino-methylene}-erythromycin-A:
9. (11S,21R)-3-decladinosyl-11,12-dideoxy-6-O-methyl-3-oxo-12,11-{oxycarbonyl-[E-(N-(2-(pyrimidin-2-yl)-1,3,4-thiadiazol-5-yl)-(S)-ethyl-1-oxy]-carboxamidino-methylene}-erythromycin-A:

10. (11S,21R)-3-decladinosyl-11,12-dideoxy-2-fluoro-6-O-methyl-3-oxo-12,11-{oxycarbonyl-[E-(N-(2-pyrimidin-2-yl)-1,3,4-thiadiazol-5-yl)-(S)-ethyl-1-oxy]-carboxamidino-methylene}-erythromycin-A:
11. (11S,21R)-3-decladinosyl-11,12-dideoxy-6-O-methyl-3-oxo-12,11-{oxycarbonyl-E-(N-[1-(5-pyrazin-2-yl-[1,3,4]-thiadiazol-2-yl)-(S)-ethyl-1-oxy]-carboxamidino-methylene}-erythromycin-A 12. (11S,21R)-3-decladinosyl-11,12-dideoxy-2-fluoro-6-O-methyl-3-oxo-12,11-{oxycarbonyl-E-(N-[1-(5-pyrazin-2-yl-[1,3,4]-thiadiazol-2-yl)-(S)-ethyl-1-oxy]-carboxamidino-methylene}-erythromycin-A:
13. (11S,21R)-3-Decladinosyl-11,12-dideoxy-6-O-methyl-3-oxo-12,11-{oxycarbonyl-[E-amino-((5-pyrimidin-2-yl)-isoxazol-3-yl-methyloxy-imino)-methylene]}-erythromycin A:
14. (11S,21R)-3-Decladinosyl-11,12-dideoxy-2-fluoro-6-O-methyl-3-oxo-12,11-{oxycarbonyl-[E-amino-((5-pyrimidin-2-yl)-isoxazol-3-yl-methyloxy-imino)-methylene]}-erythromycin A:

It is to be understood that the disclosure including the various embodiments and examples given here are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the various embodiments and examples provide further detail in connection with what are presently deemed to be the most practical and preferred embodiments of the invention.

We claim:
1. A process for preparation of a compound of Formula (IX)

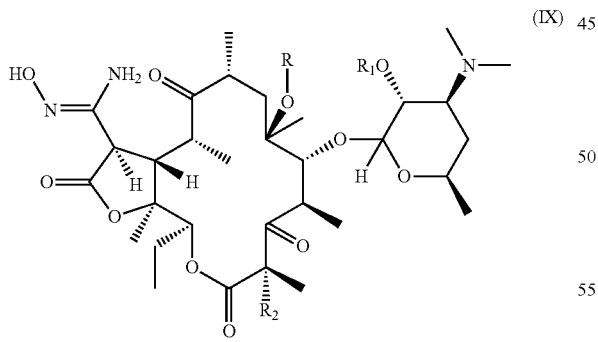

wherein,
R is $C_1$-$C_6$ alkyl;
$R_1$ is a hydroxyl-protecting group; and
$R_2$ is hydrogen or fluorine;
comprising:
(a) converting a compound of Formula (I) into a compound of Formula (II);

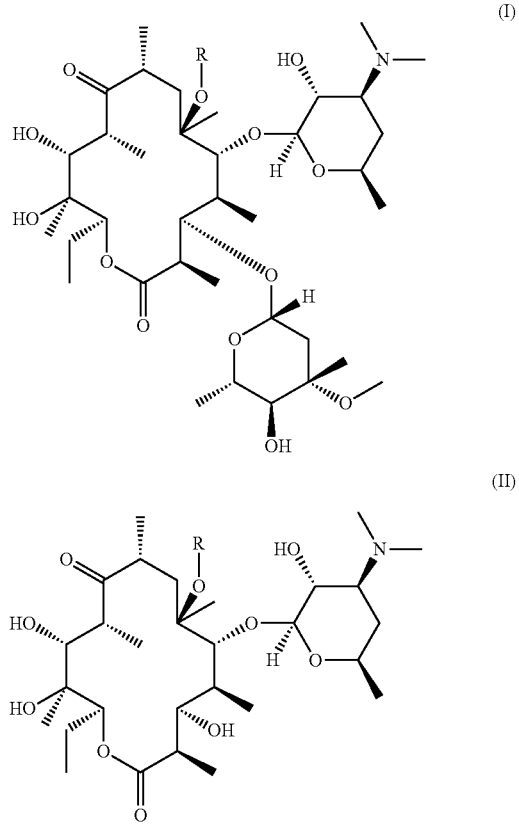

(b) converting a compound of Formula (II) into a compound of Formula (III);

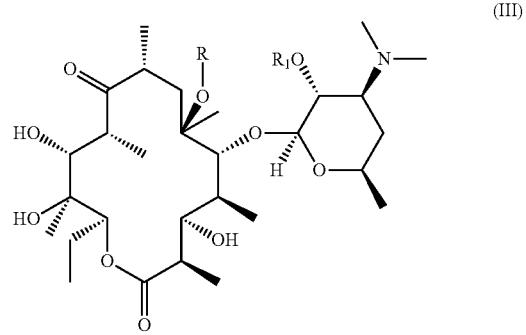

(c) converting a compound of Formula (III) into a 11,12 carbonate intermediate of Formula (IV);

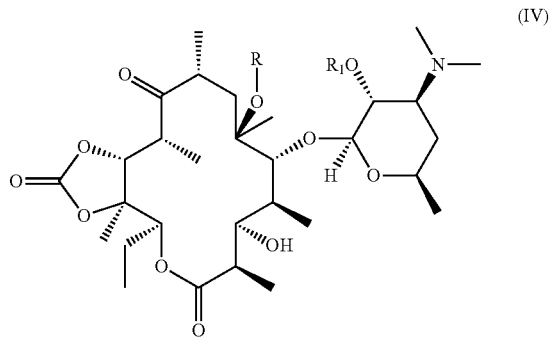

(d) oxidizing a compound Formula (IV) into a compound of Formula (V);

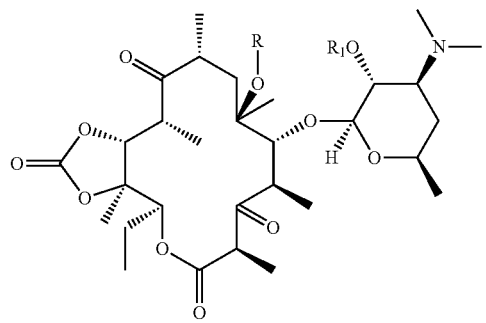

(e) converting a compound of Formula (V) into a compound of Formula (VI), wherein $R_2$ is hydrogen or fluorine;

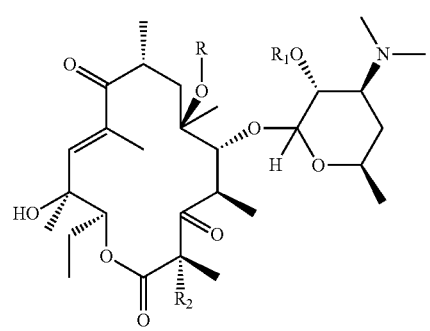

(f) reacting a compound of Formula (VI) with chloroacetic anhydride or chloroacetic acid, optionally in presence of a base, to obtain a compound of Formula (VII);

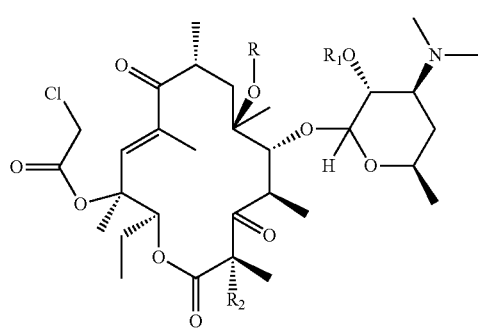

(g) reacting a compound of Formula (VII) with a cyanating agent in presence of a base, to obtain a compound of Formula (VIII); and

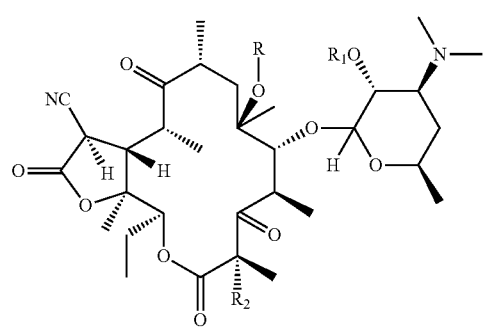

(h) reacting a compound of Formula (VIII) with hydroxylamine hydrochloride in presence of a base to obtain a compound of Formula (IX).

2. The process according to claim 1, wherein the base used in step (f) is pyridine, dimethylaminopyridine or a mixture of pyridine and dimethylaminopyridine.

3. The process according to claim 1, wherein the base used in step (g) or (h) is one or more of sodium bicarbonate, sodium carbonate, sodium hydride, sodium-t-butoxide potassium hydroxide, potassium hydride and potassium t-butoxide.

4. The process according to claim 1, wherein the cyanating agent used in step (g) is sodium cyanide, potassium cyanide, copper cyanide, or tosyl cyanide.

5. A process for preparation of a compound of Formula (IX)

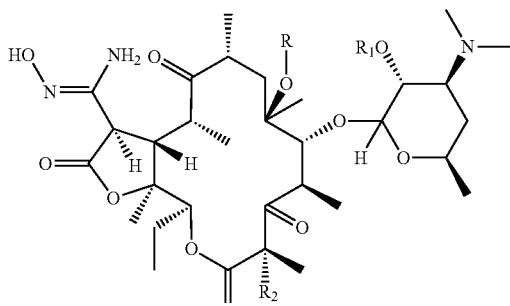

wherein,
R is $C_1$-$C_6$ alkyl;
$R_1$ is a hydroxyl-protecting group; and
$R_2$ is hydrogen or fluorine;
comprising:
(a) converting a compound of Formula (I) into a compound of Formula (II) in presence of at least one aqueous acid selected from hydrochloric acid, sulfuric acid, and phosphoric acid; and at least one solvent selected from methanol, ethanol, and isopropanol;

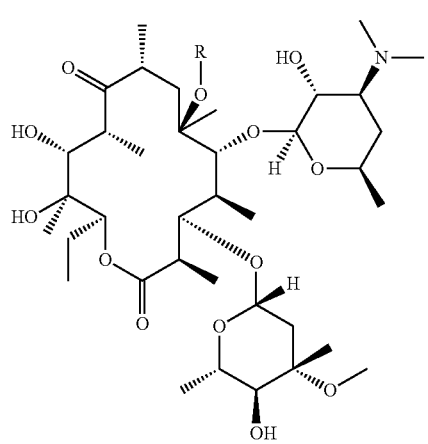
(I)

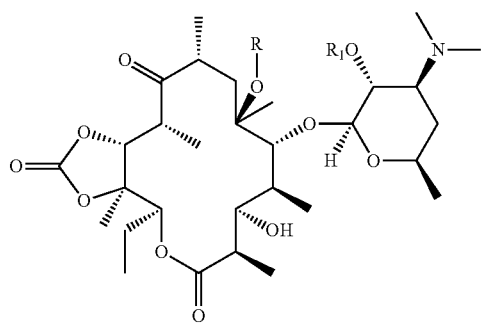
(IV)

(d) oxidizing a compound Formula (IV) into a compound of Formula (V);

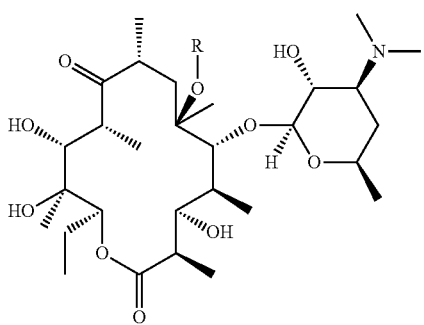
(II)

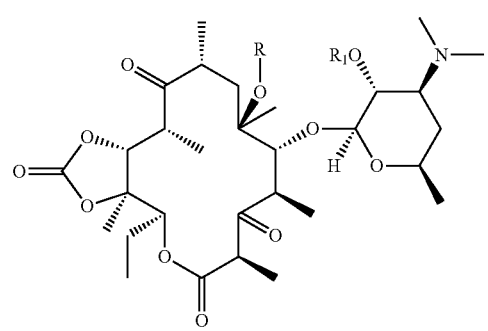
(V)

(b) converting a compound of Formula (II) into a compound of Formula (III);

(e) converting a compound of Formula (V) into a compound of Formula (VI), wherein $R_2$ is hydrogen or fluorine;

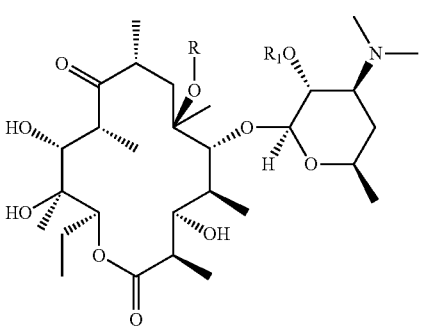
(III)

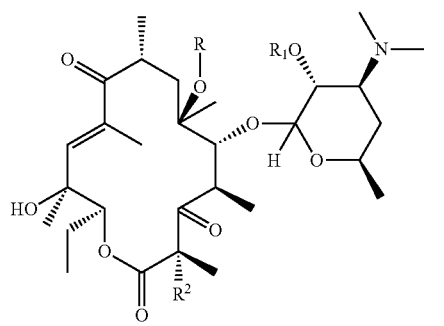
(VI)

(c) converting a compound of Formula (III) into a 11,12 carbonate intermediate of Formula (IV) in presence of triphosgene and a base, optionally in presence of a solvent;

(f) reacting a compound of Formula (VI) with chloroacetic anhydride or chloroacetic acid, optionally in presence of pyridine, dimethylaminopyridine, or a mixture of pyridine and dimethylaminopyridine to obtain a compound of Formula (VII);

(VII)

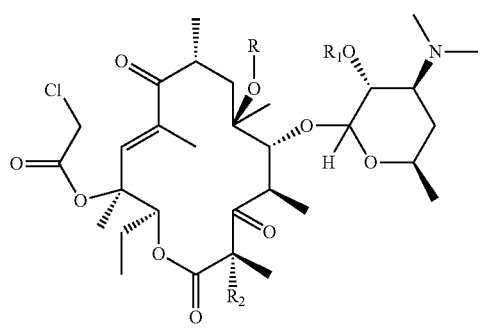

(g) reacting a compound of Formula (VII) with potassium cyanide in presence of sodium bicarbonate in dimethylformamide, to obtain a compound of Formula (VIII); and (VIII)

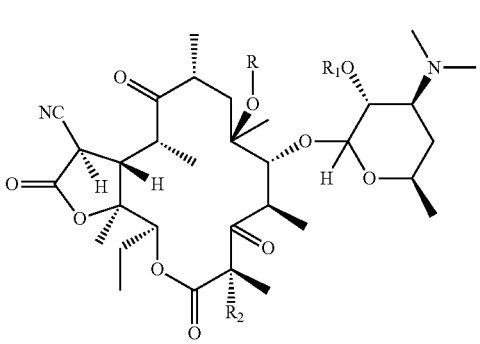

(h) reacting a compound of Formula (VIII) with hydroxylamine hydrochloride in presence of sodium bicarbonate in methanol, to obtain a compound of Formula (IX).

6. A process for preparation of a compound of Formula (XI)

(XI)

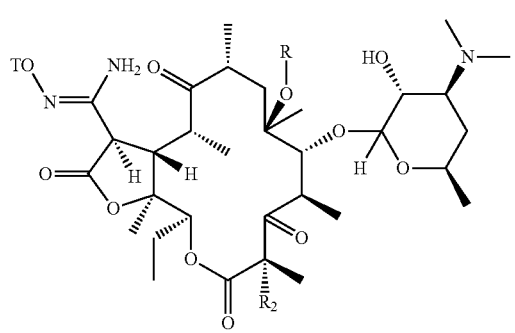

wherein,
T is —CH($R_3$)—P-Q;
$R_3$ is hydrogen, unsubstituted or substituted lower alkyl or aryl;
P is heteroaryl ring;
Q is unsubstituted or substituted aryl or heteroaryl ring;
P is attached to Q via carbon-carbon link;
R is $C_1$-$C_6$ alkyl; and $R_2$ is hydrogen or fluorine;
comprising,
(a) converting a compound of Formula (I) into a compound of Formula (II);

(I)

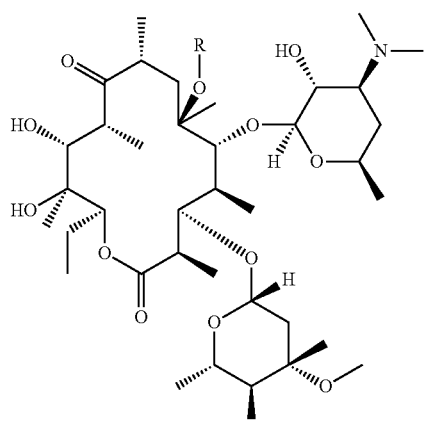

(II)

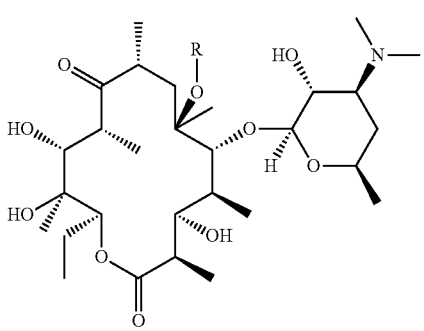

(b) converting a compound of Formula (II) into a compound of Formula (III); wherein $R_1$ is a hydroxyl-protecting group;

(III)

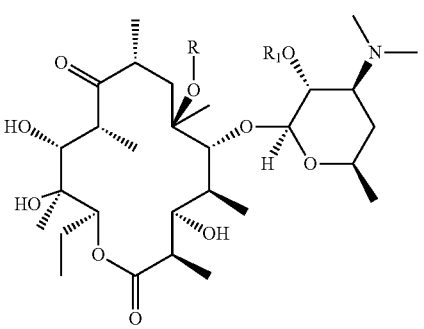

(c) converting a compound of Formula (III) into a 11,12 carbonate intermediate of Formula (IV);

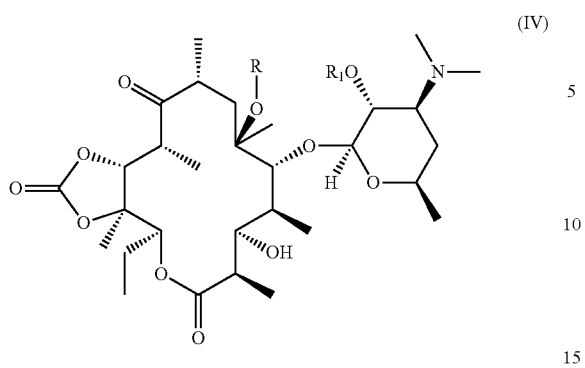

(IV)

(d) oxidizing a compound Formula (IV) into a compound of Formula (V);

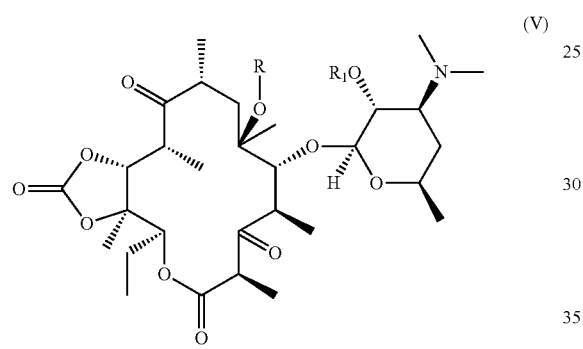

(V)

(e) converting a compound of Formula (V) into a compound of Formula (VI), wherein $R_2$ is hydrogen or fluorine;

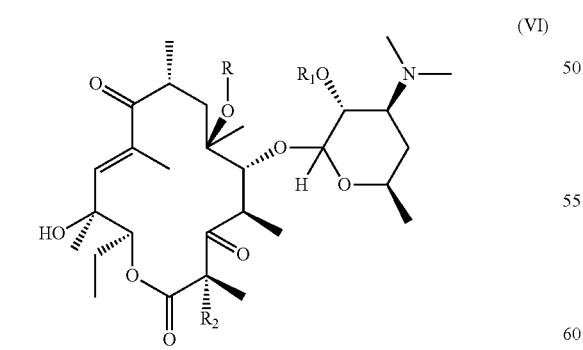

(VI)

(f) reacting a compound of Formula (VI) with chloroacetic anhydride or chloroacetic acid, optionally in presence of a base, to obtain a compound of Formula (VII);

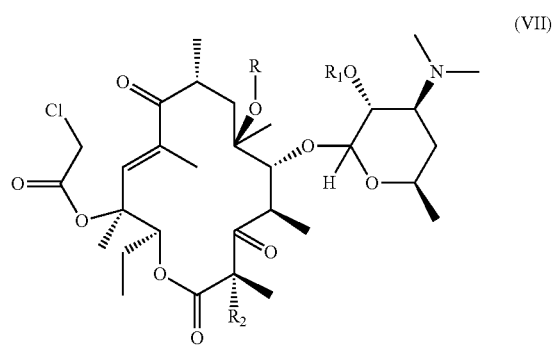

(VII)

(g) reacting a compound of Formula (VII) with a cyanating agent in presence of a base, to obtain a compound of Formula (VIII);

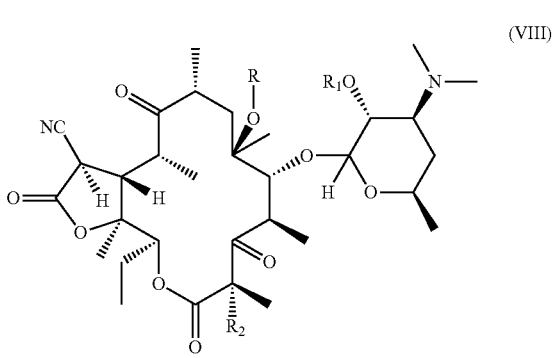

(VIII)

(h) reacting a compound of Formula (VIII) with hydroxylamine hydrochloride in presence of a base to obtain a compound of Formula (IX);

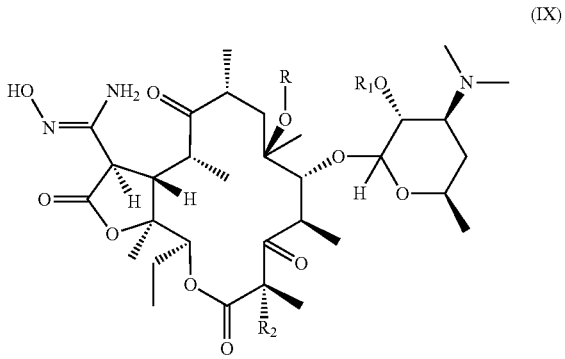

(IX)

(i) reacting a compound of Formula (IX) with compound of Formula T-Y, wherein Y is a leaving group, optionally in presence of a base, to obtain a compound of Formula (X); and

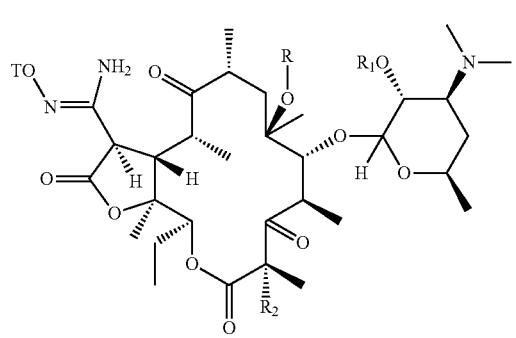
(X)

(j) reacting a compound of Formula (X) with a de-protecting agent, to obtain a compound of Formula (XI).

7. The process according to claim 6, wherein the de-protecting agent used in step (j) is selected from one or more of hydrochloric acid, sulfuric acid and pyridine hydrofluoride.

8. A process for preparation of a compound of Formula (VIb)

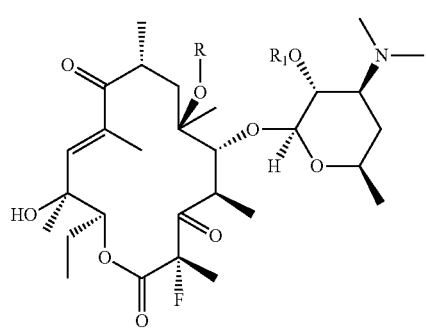
(VIb)

wherein,

R is $C_1$-$C_6$ alkyl; and $R_1$ is a hydroxyl protecting group;

comprising:

(a) converting a compound of Formula (I) into a compound of Formula (II);

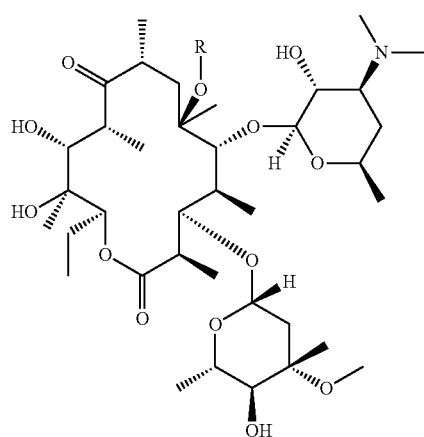
(I)

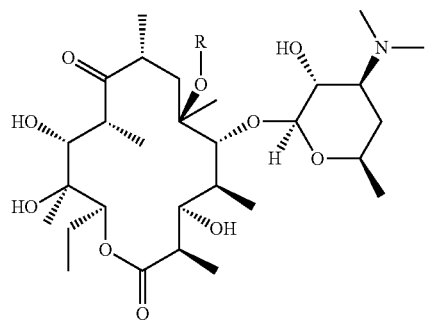
(II)

(b) converting a compound of Formula (II) into a compound of Formula (III);

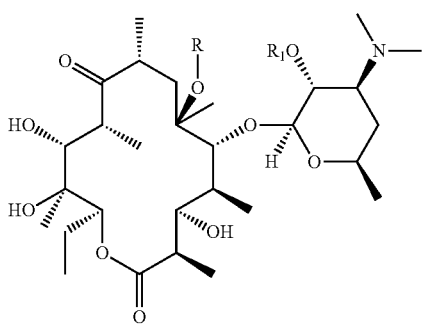
(III)

(c) converting a compound of Formula (III) into a 11,12 carbonate intermediate of Formula (IV);

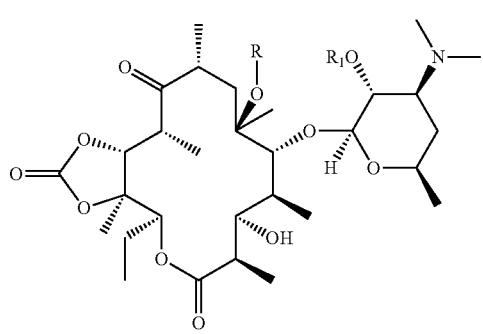
(IV)

(d) oxidizing a compound Formula (IV) into a compound of Formula (V);

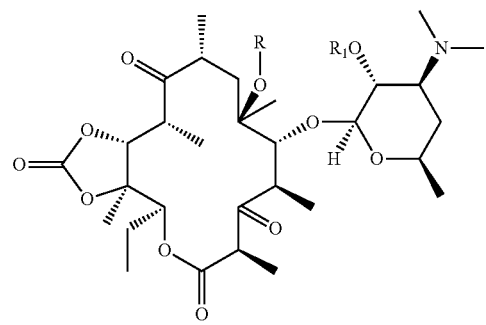
(V)

(e) converting a compound of Formula (V) into a compound of Formula (VIa); and

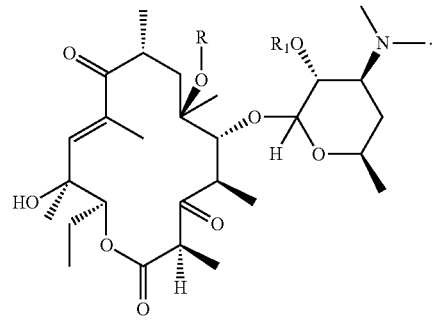
(VIa)

(f) reacting a compound of Formula (VIa) with a fluorinating agent in presence of a base and a solvent, to obtain a compound of Formula (VIb).

9. The process according to claim 8, wherein the fluorinating agent is one or more of N-fluorobenzenesulfonimide, 1-(chloromethyl)-4-fluoro-1,4 diazo bicyclo[2.2.2]octane bis [tetrafluoroborate], tetrabutylammonium fluoride and diethyl aminosulfur trifluoride.

10. The process according to claim 8, wherein the base is selected from one or more of potassium-t-butoxide, potassium hydride, sodium bis(trimethylsilyl)amide, sodium hydride and sodium-t-butoxide.

11. The process according to claim 8, wherein the solvent is one or more of dichloromethane, tetrahydrofuran, N-N-dimethylformamide and ethylene dichloride.

12. A process for the preparation of a compound of Formula (VIa)

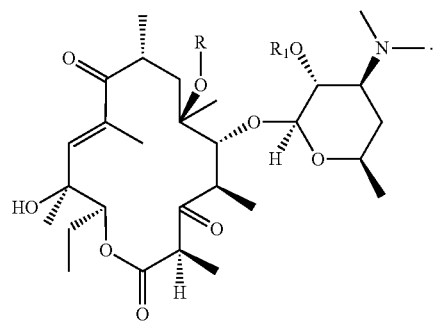
(VIa)

wherein,

R is $C_1$-$C_6$ alkyl; and $R_1$ is a hydroxyl protecting group;

comprising:

(a) converting a compound of Formula (I) into a compound of Formula (II);

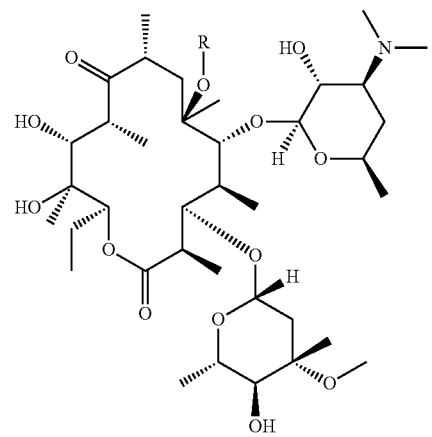
(I)

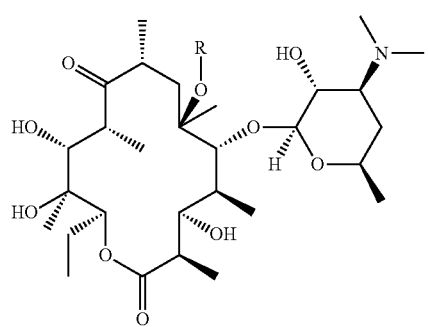
(II)

(b) converting a compound of Formula (II) into a compound of Formula (III);

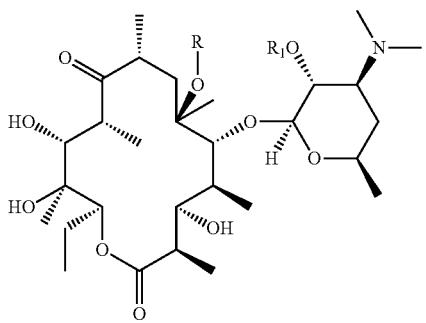
(III)

(c) converting a compound of Formula (III) into a 11,12 carbonate intermediate of Formula (IV);

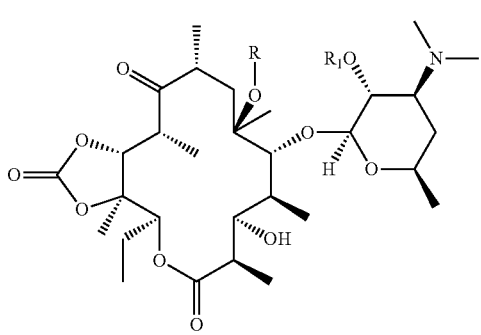
(IV)

(d) oxidizing a compound Formula (IV) into a compound of Formula (V); and

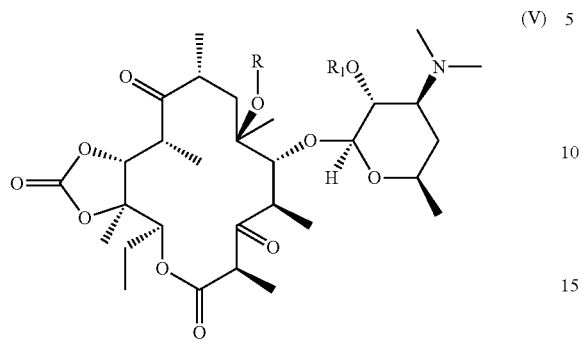

(e) converting a compound of Formula (V) into a compound of Formula (Via).

13. The process according to claim 1, wherein a compound of Formula (I) is converted into a compound of Formula (II), in presence of an aqueous acid and a solvent.

14. The process according to claim 1, wherein a compound of Formula (III) is converted into a 11,12 carbonate intermediate of Formula (IV) in presence of triphosgene and a base, optionally in presence of a solvent.

* * * * *